United States Patent [19]
Kuzma

[11] Patent Number: 5,507,303
[45] Date of Patent: Apr. 16, 1996

[54] PERCUTANEOUS CONNECTOR

[75] Inventor: Janusz Kuzma, Lane Cove, Australia

[73] Assignee: Cochlear Pty. Limited, Lane Cove, Australia

[21] Appl. No.: 157,124

[22] PCT Filed: Jun. 2, 1992

[86] PCT No.: PCT/AU92/00255

§ 371 Date: Dec. 6, 1993

§ 102(e) Date: Dec. 6, 1993

[87] PCT Pub. No.: WO92/22107

PCT Pub. Date: Dec. 10, 1992

[30] Foreign Application Priority Data

Jun. 6, 1991 [AU] Australia ................................ PK6552

[51] Int. Cl.[6] .................................................. A61B 19/00
[52] U.S. Cl. .............................. 128/899; 623/66; 607/116
[58] Field of Search .................................. 128/897–899, 128/642; 623/66; 607/116–118

[56] References Cited

U.S. PATENT DOCUMENTS

| | | | |
|---|---|---|---|
| 3,521,216 | 7/1970 | Tolegian | 339/12 |
| 3,808,577 | 4/1974 | Mathauser | 339/12 R |
| 4,025,964 | 5/1977 | Owens | 3/1 |

Primary Examiner—Angela D. Sykes
Assistant Examiner—John P. Lacyk
Attorney, Agent, or Firm—Norbert P. Holler; Gottlieb, Rackman & Reisman

[57] ABSTRACT

A connector set for percutaneous connection of an implanted device, such as an intracochlear implant, to an external system is disclosed. The connector set preferably has a base portion (30) which is adapted to be affixed to the bone structure beneath the skin and includes a male connector (1C), and a female connection (31) which is mated with and affixed externally to the male connector and is retained in contact therewith magnetically. A bias arrangement (9, 10) operates between the connector components (30, 31) so that while contact therebetween is normally firm, accidental disconnection carries a reduced risk of injury to a user.

13 Claims, 2 Drawing Sheets

PERCUTANEOUS CONNECTOR

TECHNICAL FIELD

The present invention relates to connector systems for electrically connecting implanted devices to external devices.

BACKGROUND ART

There is a need in many applications where an electrically controlled device is implanted into a living body for a connection to provide power for the device, and/or to form a link for sending information and commands to and from the device. Both transdermal and percutaneous devices have been used. The present invention is concerned with percutaneous devices. Such devices involve a surgically implanted component, and an external component.

Prior art implants, such as that described in U.S. Pat. No. 4,025,964 to Lester J. Owens, comprise a base with a cylindrical portion terminating in a rim. The base is made with a series of holes. Inside the rim is a female portion in which sits a corresponding mated plug. Two electrical connections mate with connections on the male plug. The disadvantages of prior art devices such as this include the presence of holes which provide locations and sites for the accumulation of infection and bodily fluids, and the necessity to have electrical conductors depending from the base in substantially perpendicular fashion due to the design. Such devices are only able to provide at most two to three electrical connectors. No-means is provided to secure the base to a bone structure, and further the expectation is that skin will grow around the cylindrical portion up to beneath the lower surfaces of the rim. No protection is provided for the regrown skin surfaces, which are vulnerable to damage as they cannot heal completely but only so as to abut the cylindrical portion.

It is an object of the present invention to ameliorate at least one of the disadvantages of the prior art.

DISCLOSURE OF INVENTION

According to one aspect the present invention comprises a base for a percutaneous connector set, said base being adapted to be implanted beneath a skin surface and to extend above the skin so as to provide electrical connection to an implanted device, said base comprising a lower flange, said lower flange having a generally smooth surface and being adapted to be operatively positioned beneath fine skin surface, a waist portion adapted to be operatively positioned so as to form the junction between the device and the skin surface, said waist portion having a smaller cross-sectional area than said lower flange, and an upper flange having a greater cross-sectional area than said waist portion, so as to be adapted to operatively overlie and protect the skin surface abutting the waist portion, and a connector part above said upper flange.

According to another aspect the present invention comprises a percutaneous connector set comprising a base and an external part, said base being adapted to be implanted beneath a skin surface and to extend above the skin so as to provide electrical connection to an implanted device, said base comprising a lower flange, said lower flange having a generally smooth surface and being adapted to be operatively being positioned beneath the skin surface, a waist portion adapted to be operatively positioned so as to form the junction between the device and the skin surface, said waist portion having a smaller cross-sectional area than said lower flange, and an upper flange having a greater cross-sectional area than said waist portion, so as to be adapted to operatively overlie and protect the skin surface abutting the waist portion, and a connector part above said upper flange; said external part comprising a second connector adapted to mate with said connector part.

BRIEF DESCRIPTION OF DRAWINGS

An embodiment of the present invention will now be described by way of example only with reference to the accompanying drawings in which.

DETAILED DESCRIPTION OF INVENTION

The present invention will be described with reference to a particular embodiment which is adapted for use in connecting a cochlear implant to an external device. It should be understood, however, that the invention is equally applicable to other applications with suitable modifications.

Figure 2:
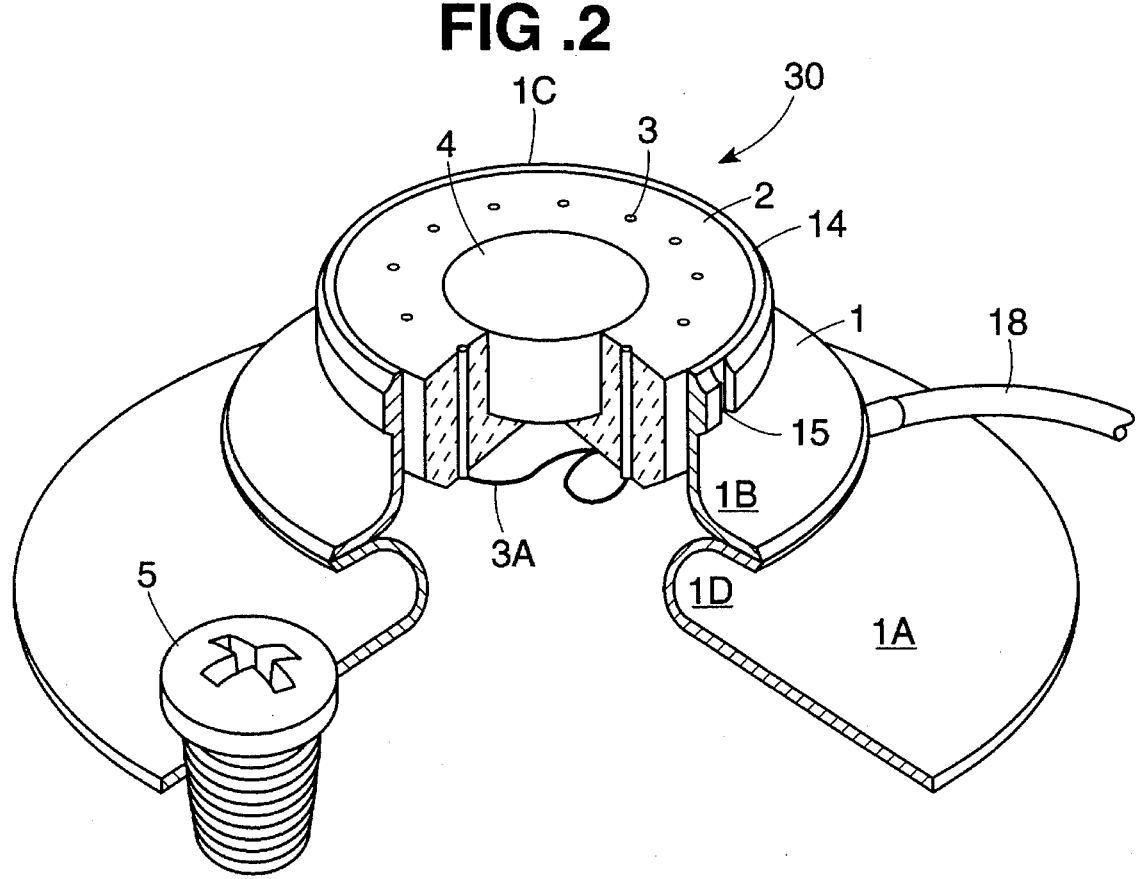
FIG. 2 is a perspective view in part section of a male connector for use with the connector of FIG. 1.

Illustrated in FIG. 2 is the implanted part 30 of the percutaneous connection device according to a preferred embodiment of the present invention, which comprises a base 1 having a lower flange 1A and an upper flange or rim 1B. Lower flange 1A is the main part of the base 1 which rests against a bone or other structure. Extending from the rim or upper flange 1B is the male connector 1C which is made up of a centrally located ceramic disk 2 through which is carried platinum a plurality of feedthroughs 3A which terminate on the surface of the ceramic disk 2 as a substantially hemispherical contacts 3, such that the highest point of the connector 30 is in fact the contactors 3. Located centrally of the ceramic disk 2 is a disk type magnet 4 which is affixed thereto. The contactors 3 pass through the ceramic disk 2 in the form of single strands of wire which ultimately become conductors which are linked to the implanted device, for instance, a cochlear implant.

The lower flange 1A is secured to a bone structure by means of screw 5, and both the flange 1A and screw 5 are of constructed of a biocompatible material, preferably titanium.

It will be understood that after surgical implantation, skin is intended to regrow around the base of the implanted part 30, in particular into recess or waist portion 1D. Protruding rim or upper flange 1B, the cross-sectional area of which is smaller than that of the lower flange 1A but larger than that of the waist portion 1D, will preferably in a successful surgical result overlie and thereby protect the regrown area and the relatively delicate implant—skin junction. The use of titanium or biologically similar materials is helpful as skin will typically regrow closely around such materials.

Figure 1:
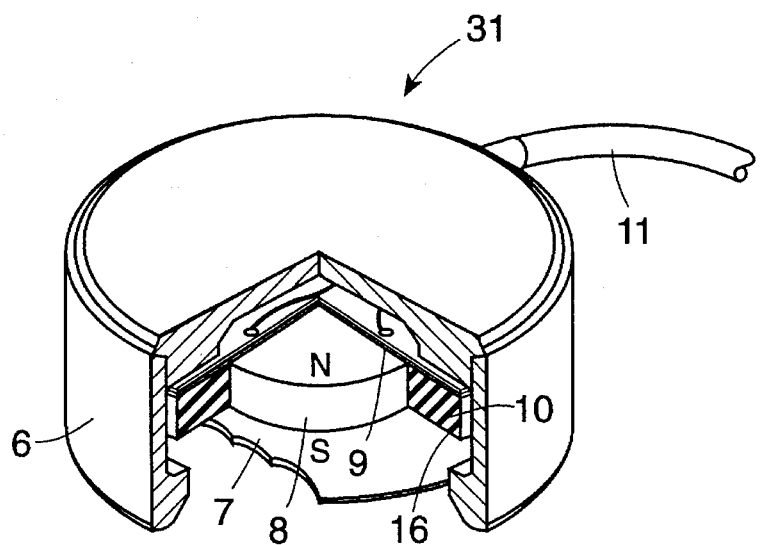
FIG. 1 is a perspective view in part section of a female connector for use with the present invention.

Around the top of the male connector 1C there is provided a rim 14 having a notch 15 for locating the female connector 31 of FIG. 1. The cavity underneath the lower flange 1A is preferably filled with a biocompatible insulating material such as adhesive silicone rubber in order to protect the implant from any body fluids which may enter therein.

Illustrated in FIG. 1 is an external female connector 31 which attaches to the male connector 1C of FIG. 2. The female connector preferably comprises a flexible pointed circuit (PC) board 7 having contactors etched thereon which are electrically connected to the wires of a cable or conductor 11. It will be appreciated that the conductor may be of any suitable type and contain as may individual connections as are required. It can be seen from FIG. 3 that PC board 7 is bent around to enable connection with conductor 11.

Sandwiched between the bent over sections of the PC board 7 is a magnet 8, which is encapsulated by an annular elastic disk 10. Overlying the magnet 8 and disk 10 is a metal plate 9 co-extensive with the full width of the elastic disk 10. This elastic disk 10 acts as a spongy bias resilient mass. All of these components are encapsulated within plug body 6. At one location corresponding to the correct alignment of the contactors 3 and the contactors of the PC board 7 is an alignment means 16 is provided for insertion in slot 15 on the male connector 1C.

Figure 3:
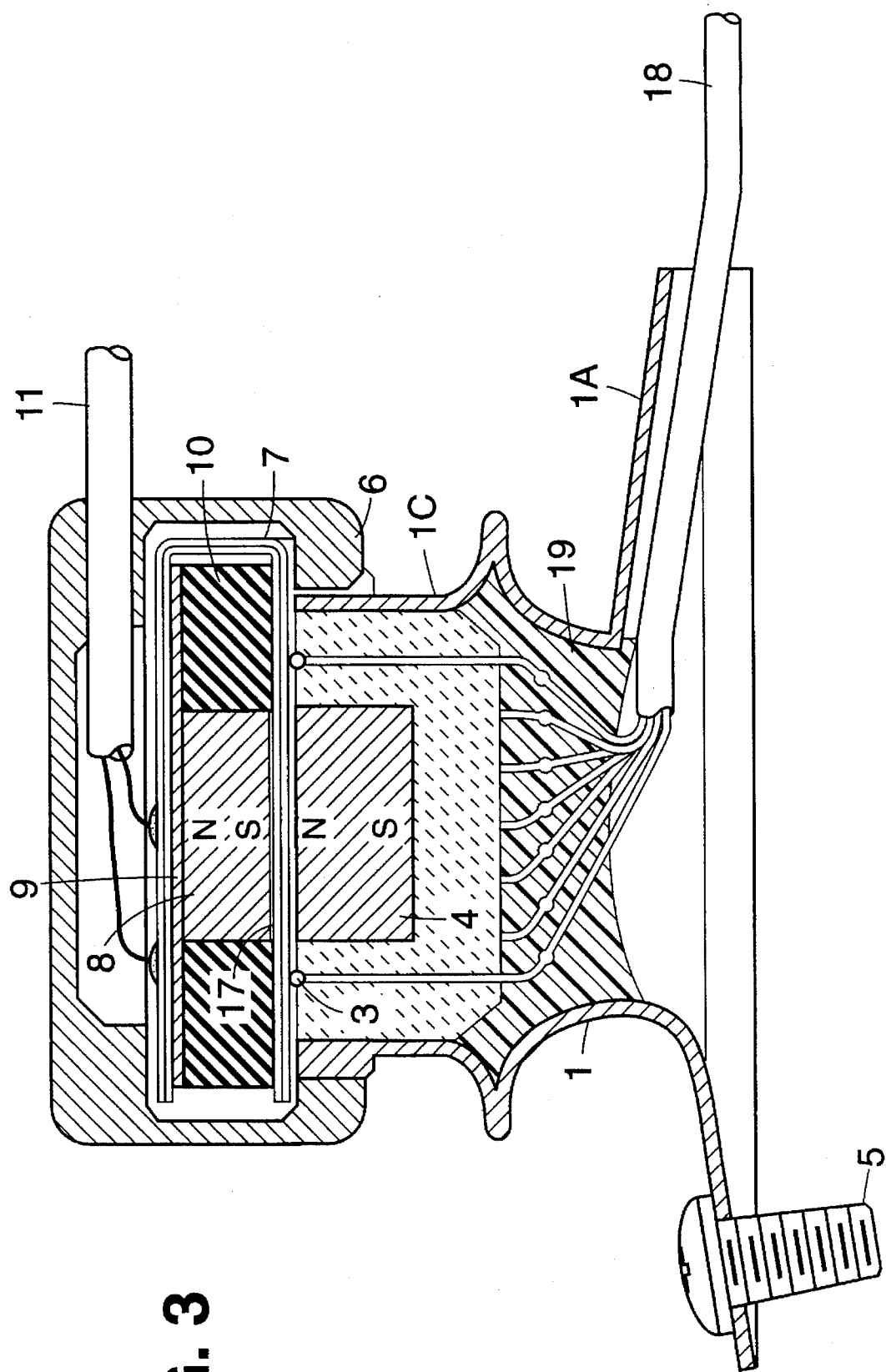
FIG. 3 is a cross-sectional view of the connectors of FIGS. 1 and 2 when joined together.

Illustrated in FIG. 3 are the connectors of FIGS. 1 and 2 in conjoined relationship. In operation the magnet 4 attracts the magnet 8, however direct contact is not made between them as is evidenced by gap 17. Whilst the gap 17 is maintained, the magnets 4 and 8 are kept in close proximity to each other, thereby maximising the magnetic field and force, without the magnets making contact.

The magnets 4 and 8 are preferably permanent rare earth magnets. The magnets 4 and 8 can never actually make contact due to the presence of PC Board 7 and the contactors 3 which protrude above the surface of the magnet 4. As the metal plate 9 is permanently and mechanically attached to magnet 8 magnet 4 attracts both magnet 8 and plate 9, thereby compressing silastic annular disk or ring 10 which in turn forces the lower end of PC board 7 into contact with the contactors 3 which protrude above the level of ceramic disk 2. This arrangement ensures that no contact is made between the magnet 4 and magnet 8; thus the force between them is reduced from the maximum possible, but is still sufficient to hold the two connectors together.

This arrangement allows the male and female components 30, 31 to separate relatively easily when a force is applied to the cable or conductor 11. This arrangement reduces the likelihood of forced removal of the implanted component 30 during accidental contact. The lower flange 1A has provision for radial entry of the cable 18 and the components of the male connector are protected by means of silicone plug 19.

It will be appreciated that any suitable surgical technique may be used to install the implanted component, as would be well understood by those skilled in the art.

The foregoing describes one embodiment of the present invention and modifications by those skilled in the an can be made thereto without departing from the scope of the present invention.

I claim:

1. A base for a percutaneous connector set, said base being adapted to be implanted beneath a skin surface and to extend above the skin so as to provide electrical connection to an implanted device, said base comprising a lower flange and having a lower side, said lower flange having a generally smooth surface which is continuous and essentially imperforate throughout its expanse, said lower flange further being adapted to be operatively positioned beneath the skin surface and including means adapted to affix said base to a bone structure beneath the skin, a waist portion adapted to be operatively positioned so as to form the junction between the device and the skin surface, said waist portion having a smaller cross-sectional area than said lower flange, and an upper flange having a greater cross-sectional area than said waist portion, so as to operatively overlie and protect the skin surface abutting the waist portion, and a connector part above said upper flange.

2. A base according to claim 1, wherein the base includes a cavity on its lower side, said cavity being filled with a biocompatible insulating material.

3. A base according to claim 2, wherein the biocompatible insulating material is a silicone rubber.

4. A base according to claim 1, wherein said base permits radial entry of the electrical connection to said implanted device.

5. A base according to claim 1, said base further including a magnetic material.

6. A percutaneous connector set comprising a base and an external part, said base being adapted to be implanted beneath a skin surface and to extend above the skin so as to provide electrical connection to an implanted device, said base comprising a lower flange and having a lower side, said lower flange having a generally smooth surface which is continuous and essentially imperforate throughout its expanse, said lower flange further being adapted to be operatively positioned beneath the skin surface and including means adapted to affix said base to a bone structure beneath the skin, a waist portion adapted to be operatively positioned so as to form the junction between the device and the skin surface, said waist portion having a smaller cross-sectional area than said lower flange, and an upper flange having a greater cross-sectional area than said waist portion, so as to operatively overlie and protect the skin surface abutting the waist portion, and a connector part above said upper flange;

said external part comprising a second connector adapted to mate with said connector part.

7. A percutaneous connector set as claimed in claim 6, wherein the base includes a cavity on its lower side, said cavity being filled with a biocompatible insulating material.

8. A percutaneous connector set as claimed in claim 7, wherein the biocompatible insulating material is a silicone rubber.

9. A percutaneous connector set as claimed in claim 6, wherein said base permits radial entry of the electrical connection to said implanted device.

10. A percutaneous connector set as claimed in claim 6, wherein said base further includes a magnetic material.

11. A percutaneous connector set as claimed in claim 10, wherein said external part comprises a second magnetic material, and compressible bias means carried by said external part at a location disposing said bias means between said external part and said connector part when the same are mated with each other, whereby upon said external part and said base being operatively conjoined by the mating of said external part and said connector part, said bias means is compressed so as to reduce the force required to separate said external part and said base.

12. A base for a percutaneous connector set, said base being adapted to be implanted beneath a skin surface and to extend above the skin so as to provide electrical connection to an implanted device, said base comprising a lower flange, said lower flange having a generally smooth surface which is continuous and essentially imperforate throughout its expanse, said lower flange further being adapted to be operatively positioned beneath the skin surface, a screw extending through said lower flange and adapted to affix said base to a bone structure beneath the skin, a waist portion adapted to be operatively positioned so as to form the junction between the device and the skin surface, said waist portion having a smaller cross-sectional area than said lower flange, and an upper flange having a greater cross-sectional area than said waist portion, so as to operatively overlie and protect the skin surface abutting the waist portion, and a connector part above said upper flange.

13. A percutaneous connector set comprising a base and an external part, said base being adapted to be implanted beneath a skin surface and to extend above the skin so as to provide electrical connection to an implanted device, said base comprising a lower flange, said lower flange having a generally smooth surface which is continuous and essentially imperforate throughout its expanse, said lower flange further being adapted to be operatively positioned beneath the skin surface, a screw extending through said lower flange and adapted to affix said base to a bone structure beneath the skin, a waist portion adapted to be operatively positioned so as to form the junction between the device and the skin surface, said waist portion having a smaller cross-sectional area than said lower flange, and an upper flange having a greater cross-sectional area than said waist portion, so as to operatively overlie and protect the skin surface abutting the waist portion, and a connector part above said upper flange;

said external part comprising a second connector adapted to mate with said connector part.

* * * * *